United States Patent [19]

Cox

[11] Patent Number: 5,239,873
[45] Date of Patent: Aug. 31, 1993

[54] FLEXIBLE SEAL REMOVAL RESISTANCE TESTER

[75] Inventor: Gary B. Cox, Philo, Ill.

[73] Assignee: Kraft General Foods, Inc., Northfield, Ill.

[21] Appl. No.: 810,482

[22] Filed: Dec. 19, 1991

[51] Int. Cl.$^5$ ............................................. G01N 3/24
[52] U.S. Cl. ................................................ 73/845
[58] Field of Search ................ 73/826, 827, 831, 834, 73/835, 837, 856, 150 A, 159, 842, 845

[56] References Cited

U.S. PATENT DOCUMENTS

| | | | |
|---|---|---|---|
| 3,572,108 | 3/1971 | McShane et al. | 73/141 |
| 3,580,065 | 5/1971 | Strittmater et al. | 73/150 |
| 4,194,392 | 3/1980 | Lombard et al. | 73/150 A |
| 4,856,325 | 8/1989 | Tomita et al. | 73/150 A |
| 4,856,342 | 8/1989 | Bottenbruch et al. | 73/827 |
| 4,862,740 | 9/1989 | Lanier | 73/150 A |
| 4,888,985 | 12/1989 | Siemer | 73/842 |
| 4,893,503 | 1/1990 | Kimura et al. | 73/150 A |
| 4,934,185 | 6/1990 | Nishiyama et al. | 73/105 A |
| 4,958,521 | 9/1990 | Morimoto et al. | 73/827 |

FOREIGN PATENT DOCUMENTS

| | | |
|---|---|---|
| 1948897 | 4/1971 | Fed. Rep. of Germany . |
| 2720536 | 6/1977 | Fed. Rep. of Germany . |
| 3010054 | 11/1980 | Fed. Rep. of Germany ........ 73/835 |
| 0033612 | 3/1980 | Japan ................................. 73/845 |
| 1019297 | 5/1983 | U.S.S.R. ............................ 73/150 A |

OTHER PUBLICATIONS

4-Page information brochure from VE, Inc. Packaging and Automation entitled, "Seal Strength Tester for Rigit and Flexible Packages".

*Primary Examiner*—Robert Raevis
*Attorney, Agent, or Firm*—Fitch, Even, Tabin & Flannery

[57] ABSTRACT

A method and apparatus for testing the force required to remove flexible seals from objects such as product cups is disclosed. The object, e.g., cup is held so that the seal defines a substantially horizontal plane and a portion of the flexible seal is attached to a force measuring gripper. The object, e.g., cup is then moved away from the gripper at an angle $\theta/2$ with respect to horizontal. Forces are then measured by the gripper at an angle $\theta$ from horizontal. In a particular example, $\theta$ equals 45° which simulates human removal of the flexible seal. The measured forces are digitized and stored for report generation.

6 Claims, 9 Drawing Sheets

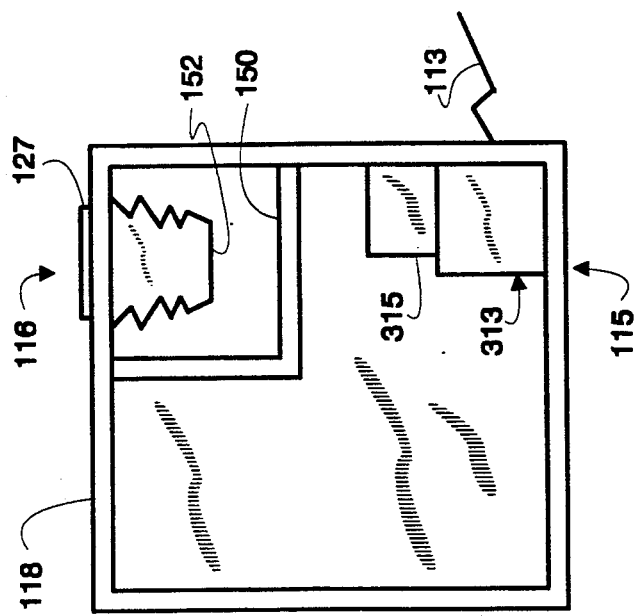
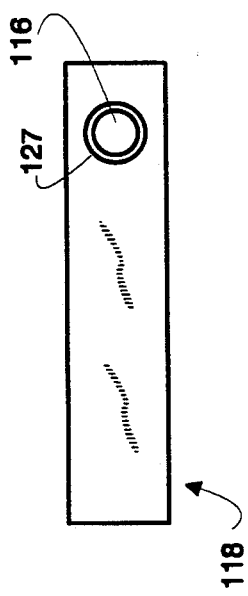
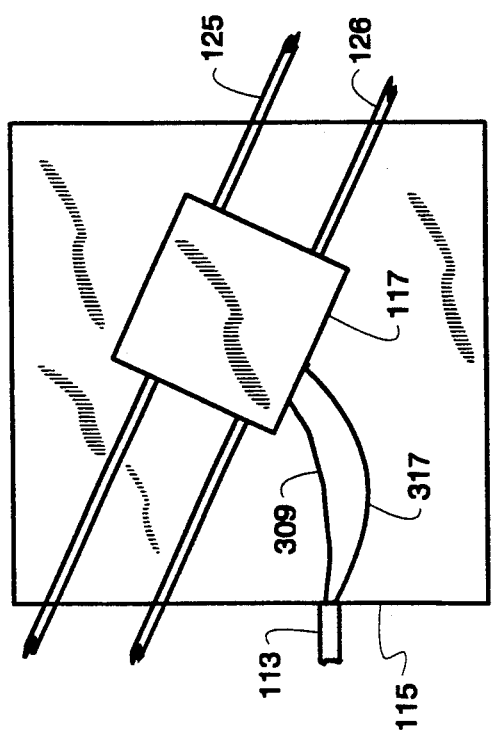

FLEXIBLE SEAL REMOVAL RESISTANCE TESTER

FIELD OF THE INVENTION

This invention relates to a method and an apparatus for the measurement of forces required in the removal of a flexible seal membrane from objects to which they are attached. More specifically, the invention is directed to an improved method and apparatus for measuring the force required to remove a flexible seal from a container at a predetermined angle.

BACKGROUND OF INVENTION

In the packaging industry, improved techniques for sealing products into containers are continually being sought. The product can be almost anything which will fit into containers, such as screws, fasteners, or food products. Oftentimes, a membrane or flexible seal is affixed to the product container, forming a seal which protects the product or retains the product within the container. When it is desired to use the product, the flexible seal must be removed by the consumer. The force required to remove the seal is important. If too much force is required, the consumer will have great difficulty opening the product container, leading to consumer dissatisfaction. On the other hand, the seal must be secured with sufficient strength so that the product is held within the container and, in the case of food product, protected from spoilage.

The flexible seal is typically attached to the container by packaging equipment. The strength of the bond between the seal and the container is determined by adjustments which are performed on the packaging equipment. For instance, the amount and type of adhesive applied to a seal are factors affecting the strength of the seal-container bond. If the bond is formed by means of heat, the amount and distribution of applied thermal energy will govern the strength of the bond.

During initial set-up of the packaging equipment, it is desirable to test the force required to remove the seal from the container so that the proper seal removal forces can be achieved. Periodic testing is also desirable so that the packaging equipment can be adjusted for operation within specified parameters. Thus, there is a need for an accurate way of measuring seal removal forces.

Apparatus for measuring seal removal forces is known in the art. One prior arrangement, disclosed in Kimura et al., U.S. Pat. No. 4,893,503 measures the force required to remove a seal from a container along a line parallel to the surface of the seal. The force measured parallel to the seal surface does not, however, accurately represent the force required at the angle of seal removal most often used by consumers. Consumer removal forces are more accurately measured at an angle of approximately 45° with respect to the seal surface.

Another prior arrangement disclosed in U.S. Pat. No. 4,958,521, issued to Morimoto et al., measures forces required to remove a flexible seal from a tape-like product at an angle simulating consumer removal. The Morimoto et al. arrangement, however, requires complex mechanisms, such as precisely configured bevel gears which move both the product and the flexible seal in order to achieve a consistent removal angle. The complexity of such apparatus increases its expense, and renders maintenance and operation relatively difficult.

Flexible seals are often employed in the food preparation industry to affix a removable seal over a cup containing a liquid or semi-liquid food product. Handling such liquids in a packaging environment is somewhat more complex than handling solid products. Prior force measuring devices often employ mechanical clamps for retaining the container being tested. These clamps, if used with a liquid product, may provide adequate retention for seal removal, but in practice, the container is often punctured, or the product is often spilled, resulting in time-consuming cleanup of the apparatus.

A need exists in the art for a device which measures the removal forces of flexible seals at an angle simulating consumer removal, while avoiding the complexity of prior arrangements. A need also exists for apparatus which holds containers while seal removal forces are being measured in such a manner that product spillage or leakage is avoided.

SUMMARY OF THE INVENTION

A flexible seal removal force measuring apparatus in accordance with the present invention measures seal removal forces in a manner simulating consumer seal removal without the complexity of prior arrangements. Additionally, holding apparatus is provided for holding the object to which the seal is attached, which apparatus can readily be used with liquid-filled containers without risk of liquid leakage or spillage. The removal forces can be repeatedly measured by the apparatus during the seal removal so that removal forces applied along the entire seal can be incrementally reported. Advantageously, signals representing the removal forces are stored in a computer memory of the apparatus so that force removal reports can be generated after force measurement is completed.

The apparatus of the preferred embodiment is primarily used to measure removal forces for an object having a flexible seal adhered thereto such that the seal is situated substantially in a plane. Advantageously, the apparatus removes the flexible seal from an object and measures seal removal forces at a predetermined angle $\theta$ to the plane of the seal which simulates the removal of the seal by consumers. A fastener is used to affix a non-adhered portion of the seal to a stationary portion of the apparatus. The object is moved away from the fastener in a substantially straight line at one-half the predetermined angle ($\theta/2$) with reference to the plane of the seal. In this manner, the flexible seal is removed from the object at the predetermined angle ($\theta$) with reference to the plane of the seal to simulate consumer removal.

The seal removal force may be measured over a period of time to determine the manner in which the magnitude of the force changes over time. Similarly, the removal force may be measured over distance to determine the magnitude of the force at various points along the seal. The object may be moved at a constant velocity, and the measurements conducted at regular time intervals, to achieve measurement of the force at equal distances along the seal.

The force measurement apparatus may include a force gauge connected to the fastener for generating signals representative of forces at the angle $\theta$ from the plane of the seal. Signal-sampling circuitry may be employed to periodically sample the output of the force gauge during motion of the object. The force gauge may include digital circuitry for generating digital signals representative of force, and/or digital sampling circuitry for processing the output signal from the force gauge. The digital signals may be stored in a memory for subsequent processing and/or display.

In the embodiment the object is held in place by applying a vacuum to the object. The vacuum is applied substantially in the direction normal to the plane of the seal. The vacuum acts upon the outer perimeter of the object.

The method of the present invention permits the measurement of a force at a predetermined angle $\theta$. The angle $\theta$ is selected such that a portion of the flexible seal will be removed from the object upon the application of a force on the seal relative to the object. A force-measuring device is attached to a non-adhered portion of the seal. Next, the object is moved away from the force measuring device linearly, at a predetermined rate, and at an angle ($\theta/2$) equal to half of the predetermined angle $\theta$. The tensile force applied to the force measuring device by the seal is determined at the predetermined angle $\theta$.

The method provides for the measurement of the tensile force applied to the force measuring device by the seal over a time interval to determine the manner in which the magnitude of the force varies over time.

BRIEF DESCRIPTION OF THE DRAWINGS

FIG. 4 is a top plan view of a cup moving apparatus of FIG. 1;

FIG. 5 is a front view of the cup moving apparatus showing internal features thereof;

FIG. 9 is a rear view of the cup moving apparatus showing the attachment of an air cylinder thereto;

DETAILED DESCRIPTION OF THE PREFERRED EMBODIMENT

Figure 1:
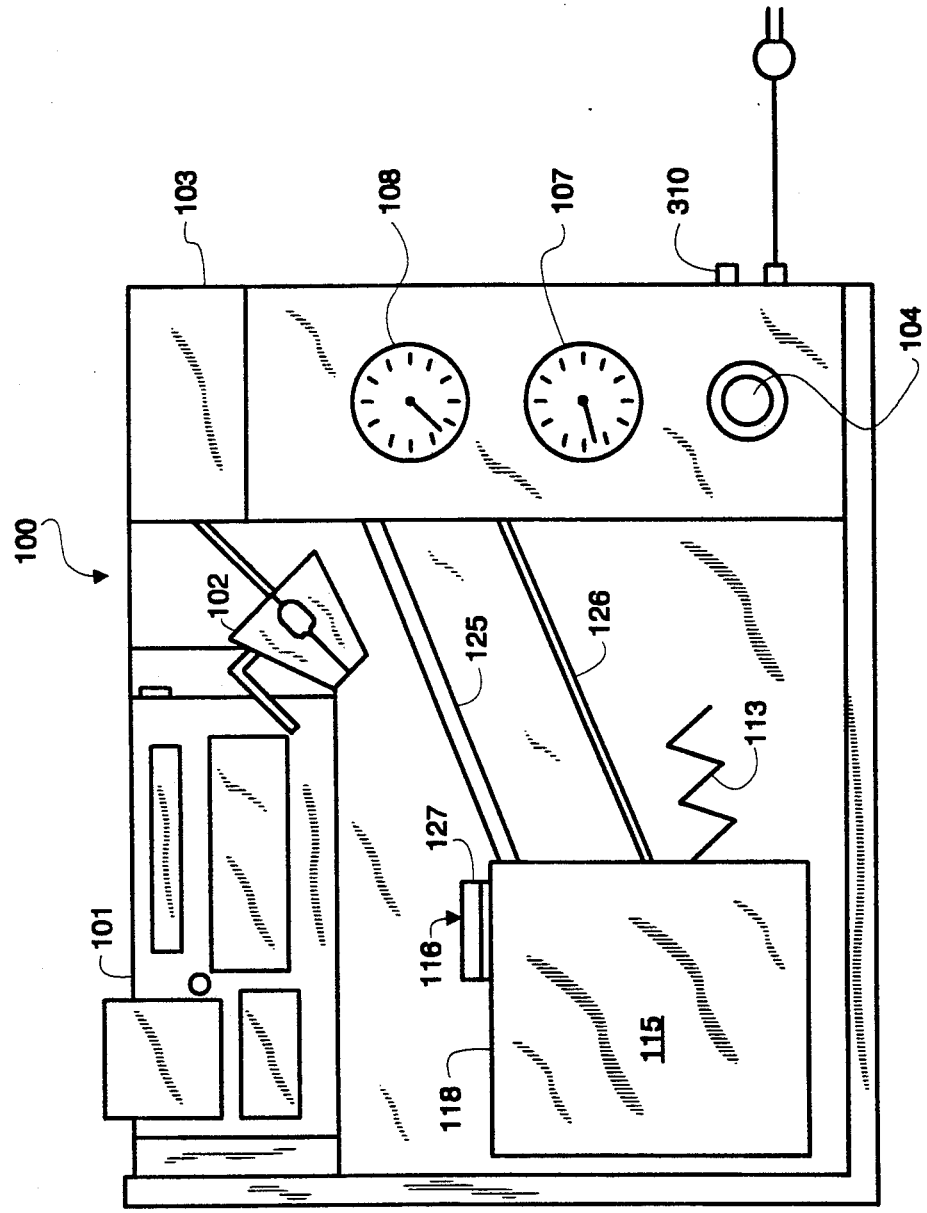
FIG. 1 is a pictorial representation in front view showing a general construction of the apparatus for measuring seal removal forces according to one embodiment of the present invention.
Figure 2:
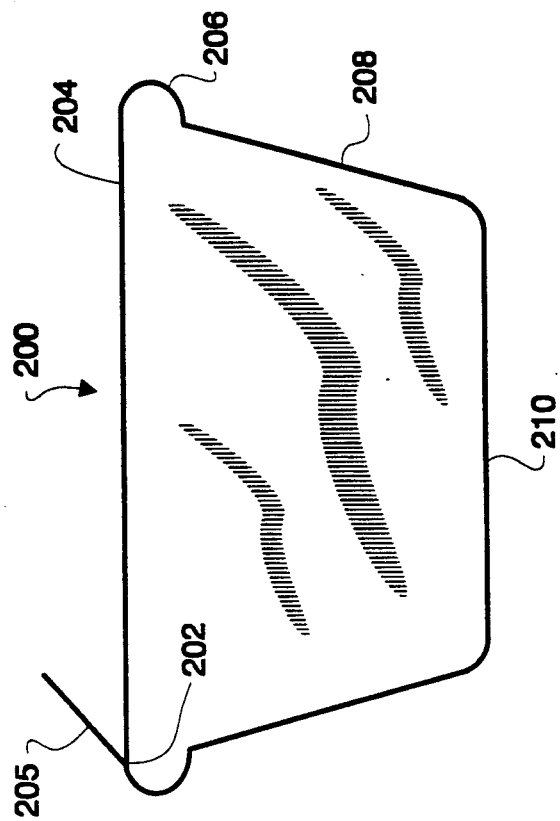
FIG. 2 is a side view of a product containing cup sealed with a flexible seal.
Figure 3:
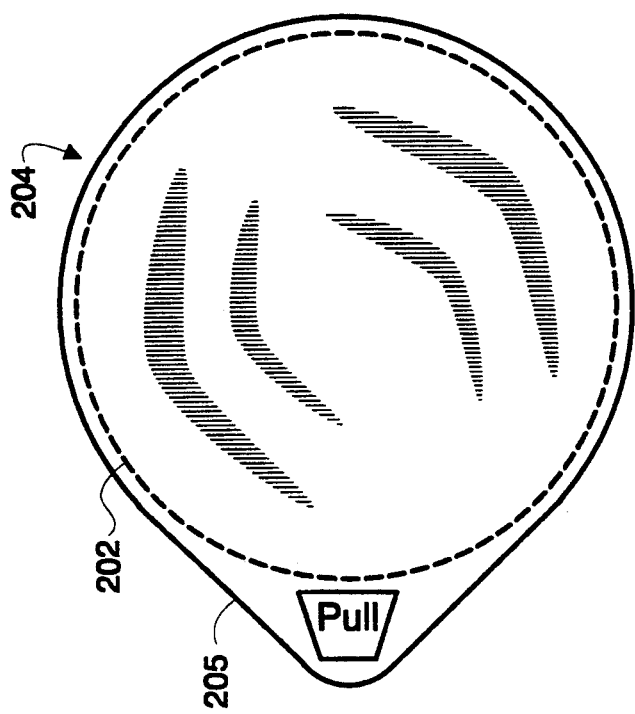
FIG. 3 is a top view of a removable flexible seal showing its attachment to the rim of the cup of FIG. 2.

FIG. 1 shows a testing apparatus 100 for testing forces required to remove flexible seals from product cups such as product cup 200 shown in FIGS. 2 and 3. Cup 200 is constructed of thermo-formed polypropylene and has a continuous sidewall 208 and bottom 210. Product, such as a liquid food product, is placed into and removed from cup 200 through a circular opening 202, which forms a plane across the top of the cup. A protrusion 206 is formed around the top of the cup to flexibly extend the exterior diameter. In the present embodiment, the opening 202 is approximately 2¾ inches in diameter, while outer the diameter of the protrusion 206 is approximately 3 inches.

FIG. 3 is a top view of a cup 200 to which a flexible seal 204 is affixed. Seal 204 is made from flexible aluminum/polymer lid stock and is adhered to opening 202. In FIG. 3, the opening 202 is shown in dotted line "through" lid 204. Lid 204 includes a non-adhered extension 205 which can be used by a consumer to grip the lid for removal from the cup. In FIG. 2, the extension 205 is bent back over the top 204 of cup 200 in preparation for testing.

Testing apparatus 100 includes a stationary framework (not numbered) for maintaining the special and angular relationships of various parts of the apparatus. In the following discussion of angular and spacial relationships, the horizontal plane as shown in FIG. 1, is used as a reference plane. The major portion of tester 100 is a product carrying assembly 115 which is movably attached to apparatus 100 by means of a rodless band cylinder 117. In FIG. 1, only the support shafts 125 and 126 of cylinder 117 are visible. The air controlled portion of cylinder 117 is affixed to the back of product carrying assembly 115 (see FIG. 9). Band cylinder 117 is attached to apparatus 100 to provide linear motion at an angle of approximately 22.5° from horizontal in FIG. 1. The product carrying assembly 115 is rectangular solid in shape and is mounted to band cylinder 117 so that its top surface 118, which holds the cup 200, is substantially horizontal. The top surface 118 of product carrying assembly 115 is shown in greater detail in FIG. 4. Surface 118 receives a cup 200 in a circular opening 116 which is surrounded by a cup receiving collar 127. Cup receiving collar 127 has an inner diameter which is slightly less than the outer diameter of the cup just below the protrusion 206. When a cup is introduced through the opening 116 and a partial vacuum is created within product carrying assembly 115 to hold cup 200 firmly in place.

FIG. 5 shows product carrying apparatus 115 with a front surface removed. A support member 150 forms a box in the upper right-hand corner of the apparatus 115. It should be mentioned that air is free to communicate within apparatus 115 around support member 150. A bellows vacuum cup 152 is attached to opening 116 inside apparatus 115. Whenever a cup 200 is placed in opening 116 and a partial vacuum is created in apparatus 115, bellows is drawn down forming a vacuum seal between the receiving collar 127 and the cup 200. Also included within apparatus 115 are a pneumatic vacuum pump 313 and a vacuum sensing switch 315. Pump 313 and switch 315 are connected to sources of control and power via a flexible connector 113.

Apparatus 100 also includes a digital force gauge 103 attached to the apparatus framework and a flexible seal gripper (sometimes called a fastening means) 102 mounted to the force gauge 103. By the connection of the framework, force gauge 103 and gripper 102, the gripper extends downward and to its left (FIG. 1) at an angle at substantially 45° from horizontal and the force gauge measures forces along the longitudinal axis of the gripper at 45° from horizontal. The attachment of gripper 102 to the framework also places its longitudinal axis substantially in line with the center of opening 116 during the motion of cup carrying apparatus 115.

In the embodiment, the force gauge 103 is a Chattilon Model DFGR-59 and the flexible seal gripper 102 is a Chattilon clamp Model GF9.

A test sequence begins with the product carrying apparatus 115 at its lower left position, as represented in FIG. 1. A cup to be tested is placed in the collar 127 with the tab end 205 of the lid bent back as shown in FIG. 2 at a 45° angle to the plane defined by opening 202 and the attached flexible seal 204. An operator pushbutton 104 is then pressed and the product carrying apparatus moves up and to the right under the power of band cylinder 117, until the tab 205 can be inserted into gripper 102. A human operator opens the gripper 102 and fastens the tab 205 securely therein. Pushbutton 104 is again pressed, and the cup carrying apparatus 115 with cup 200 is moved down and to the left. As the cup 200 proceeds away from gripper 102, the force gauge 103 continuously provides a digital signal readout of the removal forces applied to the gripper 102 by flexible seal 204. The digital signals are sampled by the apparatus 100 and stored in a microprocessor 101. When the apparatus 115 with the cup 200 has moved far enough to have completed a test sequence, its movement stops and the hold forces (vacuum) on the cup are released. The force data read by microprocessor 101 from the force gauge 103 can then be presented in printed copy to the operator and/or additional tests can be performed on new cups and additional sets of force data recorded in the microprocessor 101 memory.

Figure 6:
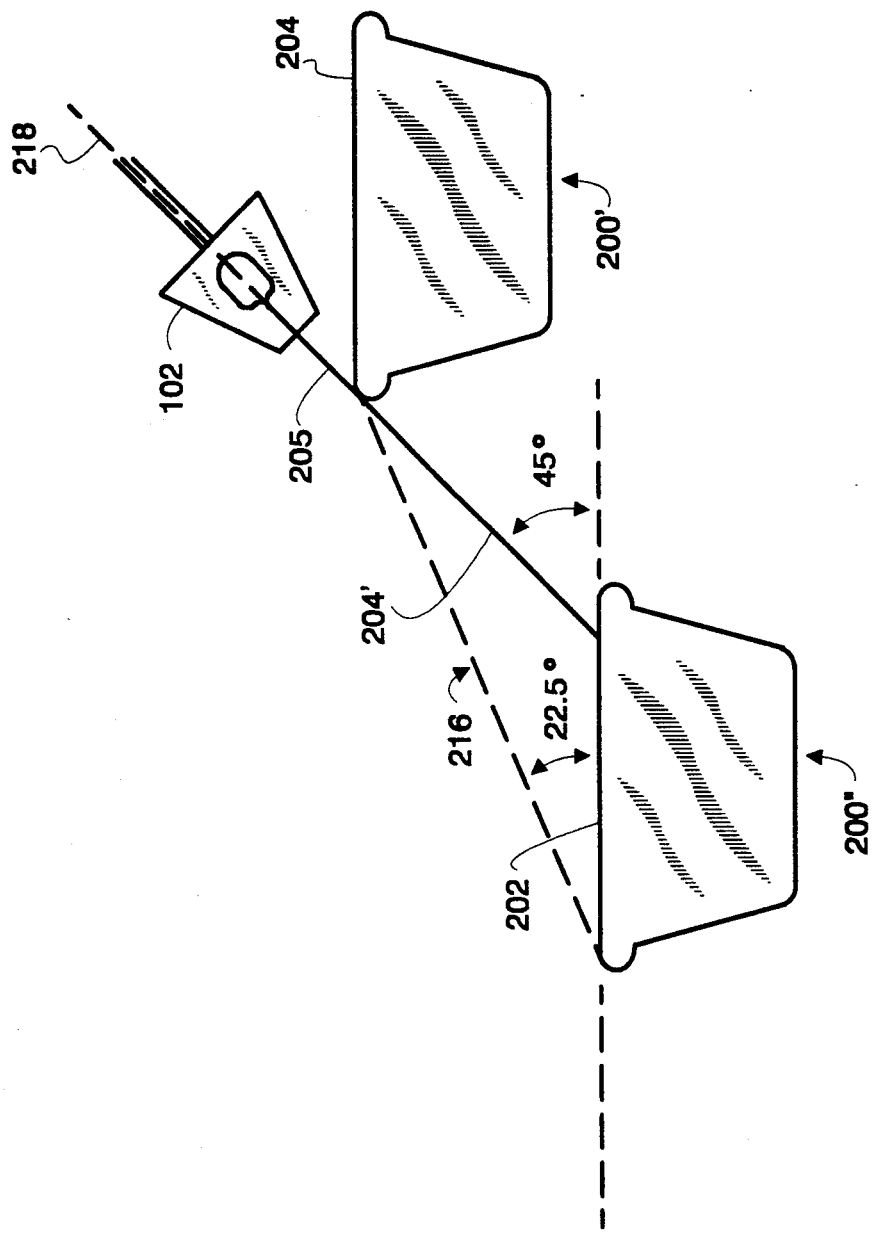
FIG. 6 is an explanatory diagram indicating the spatial relationship between the test object, the membrane gripper and the angle at which the seal removal force is measured.

FIG. 6 is a representation of cup movement during the testing function. In FIG. 6, the single cup is shown twice, once (called the first position) at the beginning of a test where it is denoted 200', and a second time (called the second position) during a test where it is denoted 200''. The angles of cup movement and force measurement are also shown with respect to the horizontal. During the test a plane defined by the top 202 of the cup is substantially horizontal. A dotted line 216 has been provided which connects a point on the leftmost of top 202 in both first 200' and second 200'' positions. From FIG. 6, it can be seen that line 216 which traces the movement of a cup 200 during a test is approximately 22.5° from horizontal. A dotted line 218 is also drawn to extend the longitudinal axis of gripper 102. Line 218 is approximately 45° with horizontal. In the first position, tab 205 runs along the 45° line 218 and is inserted into the gripper 102. As the cup moves from the first position 200' to the second position 200'' at approximately 22.5° with horizontal, the extension of top 204 as it is removed from cup 200 also lies along line 218 to provide the approximately 45° angle of flexible seal removal desired for the test. The extension of top 204 is labeled 204'. Although specifically shown for seal removal at a 45° angle, the principles of the present invention also apply to other possible angles of seal removal. When forces are to be measured at an angle $\theta$ from horizontal, the gripper 102 axis should be aligned with the angle $\theta$ and the object from which the seal is being removed should be moved at an angle equal to one-half $\theta$. In the specific example of FIG. 6, $\theta$ equals 45° and one-half $\theta$ equals 22.5°.

The apparatus 100 is controlled by a programmed logic controller PLC 250 (FIG. 7), which in the preferred embodiment is a General Electric PLC Model Number IC 609SJR100. Program logic controller 250 which is described in greater detail later herein, controls force data collection by generating a series of pulses at regular intervals during test operations. Each of the pulses identifies the time at which a seal removal force measurement is to be read from force gauge 103. The pulses are applied by controller 250 to microprocessor 101 of the apparatus 100 which responds to each pulse by reading and storing the digital output of force gauge 103. In the present embodiment, microprocessor 101 is a Mitutoyo data acquisition computer Model No. DP3DX.

Figure 7:
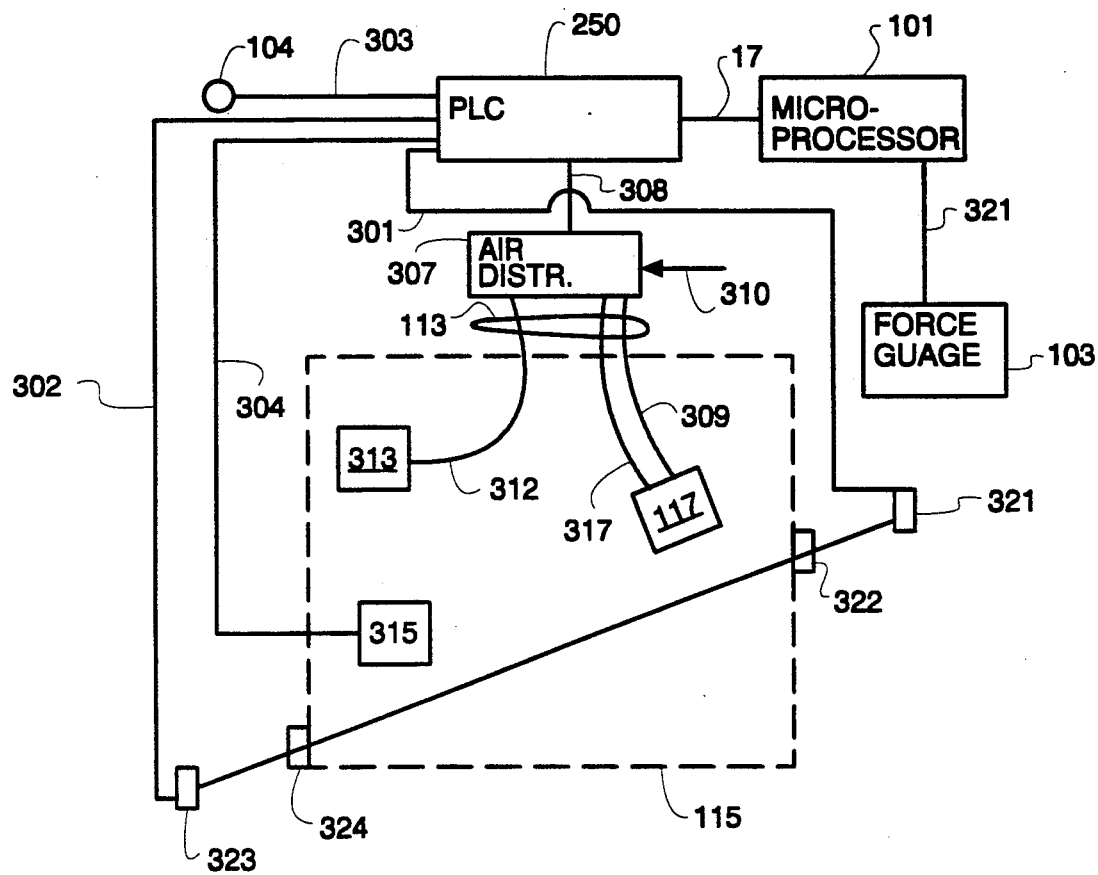
FIG. 7 is a block diagram of the electrical connections of the test apparatus of FIG. 1.
Figure 8:
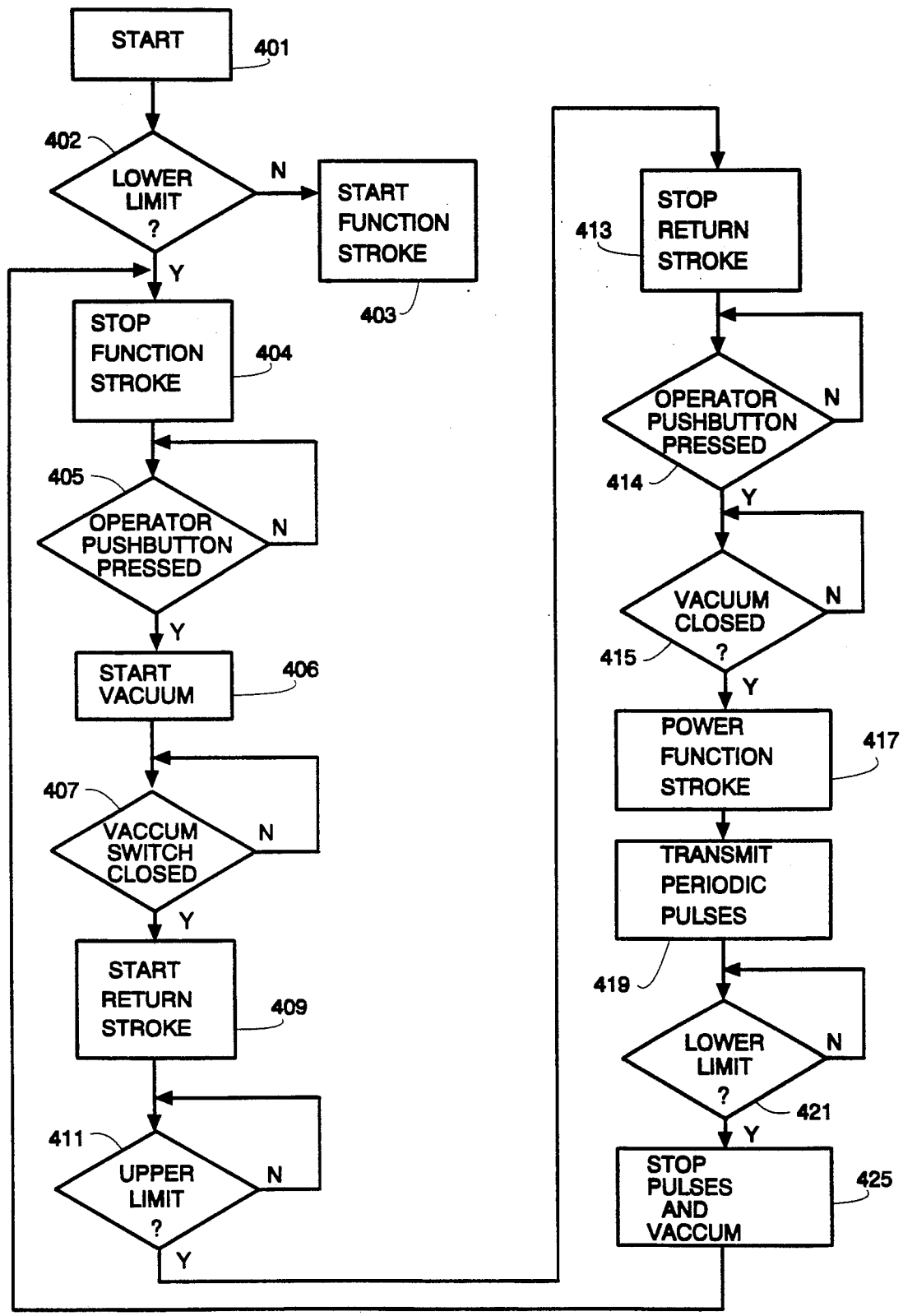
FIG. 8 is a flow diagram performed by a controller of the test apparatus of FIG. 1.

FIG. 7 is a block diagram of the electrical and air pressure connections for the control of apparatus 100 and FIG. 8 is a flow diagram of the operation of the test apparatus. To properly control testing, the apparatus includes an upper limit switch 321 and a lower limit switch 323 to identify when product carrying apparatus 115 is in its upper position ready for testing or in its lower position at test completion. In the present embodiment, upper and lower limit switches 321 and 323 are hall effect switches. To activate upper limit switch 321, a magnet 322 is attached to the product carrying apparatus 115 and a similar magnet 324 is attached to product carrying apparatus 115 to activate the lower hall effect switch 323.

When apparatus 100 is first powered up, a start step 401 (FIG. 8) is performed to initialize PLC 250. When initialization is completed, PLC 250 performs a step 402 in which it checks via a conductor 302 whether the product moving apparatus 115 is at lower limit switch 323. When lower limit switch 323 indicates that the product conveying apparatus 115 is not at is lower limit, PLC 250 in a step 403 transmits a signal via a communication path 308 to an air pressure distribution unit 307, directing that air pressure be connected via a hose 309 from an air supply input 310. Supplying air pressure to hose 309 energizes air cylinder 117 to move product carrying apparatus 115 to its lower left position. Downward movement toward limit switch 323 is called the function stroke. When limit switch 323 detects that product carrying apparatus 115 is at its lower left position, PLC 250 responds (step 402) by removing air pressure from hose 309, stopping the function stroke in a step 404. The lower left position of product carrying apparatus 115 is called home and is a normal wait state in the program. When the apparatus 115 is in the home position and an operator depresses pushbutton switch 104, a signal is sent via a conductor 303 to PLC 250. PLC 250 responds to the signal in step 405 by proceeding to a step 406 to start the vacuum pump 313 within product carrying apparatus 115. In the present embodiment, vacuum pump 313 is driven by air pressure from air distributor 307. Accordingly, in step 406 PLC 250 transmits over communication path 308, a signal directing the connection of air pressure to vacuum pump 313 via hose 312. After directing the start of vacuum, PLC 250 checks in step 407 the status of vacuum switch 315 within product carrying apparatus 115 to determine if a vacuum has been established therein.

At step 407 in the program, it is expected that a cup 200 will have been placed in the product carrying apparatus 115 and accordingly, that an adequate vacuum will be achieved within the apparatus. If no such vacuum is achieved, testing does not commence. Alternatively, when a cup has been placed in product carrying apparatus 115, the vacuum will be detected in step 407 and the programmed flow proceeds to a step 409 to move the product carrying apparatus with its cup 200 up to gripper 102. This direction of movement is referred to herein as the return stroke. To start the return stroke, PLC 250 transmits a signal over communication path 308 directing that air pressure be connected to a hose 317 connected to air cylinder 117. In response to air pressure being applied via hose 317, the product carrying apparatus moves up and to the right until limit switch 321 senses that the product carrying apparatus is in its uppermost position. The uppermost position is sensed in step 411 when the upper limit switch 321 closes. Upon sensing the closure of upper limit switch 321 in step 411, PLC 250 directs (step 413) the cessation of air pressure to hose 317 stopping the movement of the product carrying apparatus 115.

At this point in the test, the operator opens the jaws of gripper 102 and inserts the tab 205 of the flexible seal 204 therein and presses pushbutton 104. The pressing of pushbutton 104 is detected in step 414 and another check (step 415) is performed to see if vacuum still exists within product carrying apparatus 115. If vacuum is found to be present, the function stroke is powered in step 417 by applying air pressure to hose 309. Also in a step 419, PLC 250 begins to transmit a series of pulses at approximately one second intervals on a conductor 17 to microprocessor 101.

Figure 10:
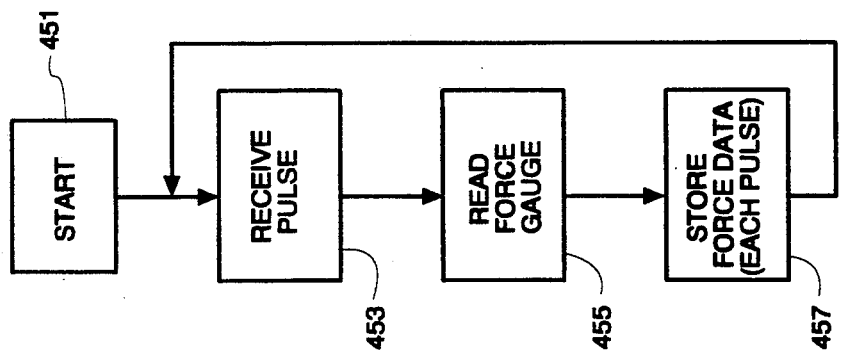
FIG. 10 is a flow diagram of the operation of a force data acquisition computer of the face testing apparatus.

By pre-adjustment of the air pressure applied via hose 309 to air cylinder 117, product carrying apparatus 117 moves in the function stroke at approximately 18 inches per minute or 0.3 inches per second. Thus, each one second pulse delivered by PLC 250 to microprocessor 101 represents the removal of between 0.2 and 0.25 inches of the flexible seal from cup 200. The operation of microprocessor 101 in response to these one second pulses is shown in the following diagram of FIG. 10. On being powered up, the first step of the microprocessor 101 sequence is an initialization step 451. It then awaits pulses from the PLC 250. Pulses are received in a step 453 and responsive to each pulse received, microprocessor 101 reads (step 455) via path 321 the output of force gauge 103. The data from the force gauge 103 is stored in a step 457 within a memory internal to the microprocessor 101. Upon storage of the data, microprocessor 101 returns to step 453 to await another pulse from PLC 250.

Pulses from PLC 250 continue to be transmitted to microprocessor 101 until product carrying apparatus 115 is detected by limit switch 323 to have completed the function stroke. The lower limit of product carrying apparatus 115 is detected in a step 421 (FIG. 8) by the closure of limit switch 323. A step 425 is then performed in which pulses from PLC 250 are terminated and signal is transmitted over communication path 308 to remove air pressure from hose 312, thereby removing the vacuum within product carrying apparatus 115. After the performance of step 425, the program flow returns to step 404 where the function stroke is stopped by removing air pressure from hose 317. At this point, the tested product cup 200 can be removed from the product moving apparatus 115 and additional tests can be performed by repeating the foregoing sequence. Upon the completion of testing, the force readings obtained in response to the one second read pulses on conductor 17 can be printed by microprocessor 101.

Figure 11:
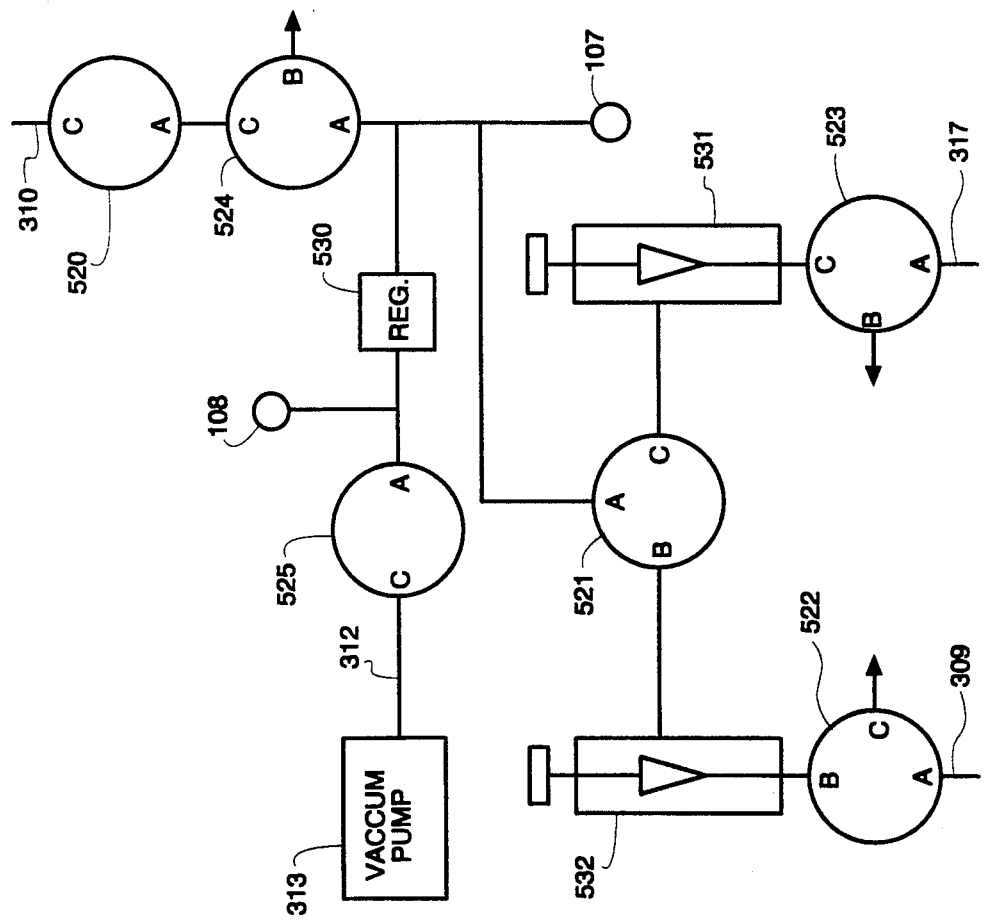
FIG. 11 is a diagram of the connection of compressed air control valves used to control the apparatus of FIG. 1.

Air distributor 307 of FIG. 7 comprises a plurality of pneumatic solenoids 520 through 525 pneumatically connected as shown in FIG. 11. Each solenoid e.g., 520 has three ports labeled A, B and C. When a solenoid e.g., 520 is not powered, its port A is connected to its port B. Alternatively, when a solenoid e.g., 520 is powered, its port A is connected to its port C. In addition to the solenoids 520 through 525, the pneumatic connection also includes pressure gauges 107 and 108, a pressure regulator 530 supplying air to solenoid 525 and a pair of manually controlled valves 531 and 532 to adjust the air pressure applied to pneumatic lines 317 and 309, respectively.

Figure 12A:
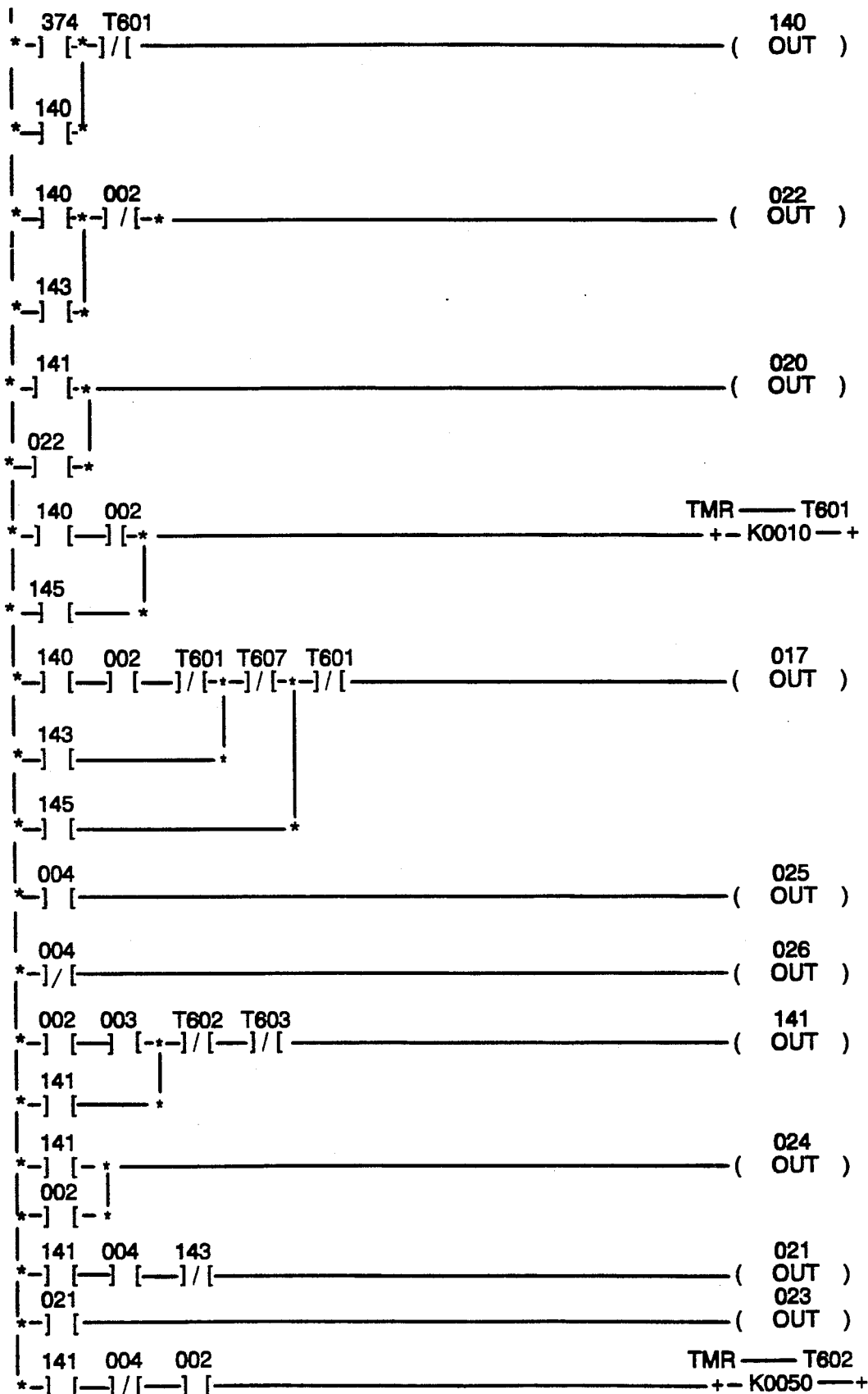
FIGS. 12A and 12B illustrate the ladder logic control program employed by a controller of the apparatus of FIG 1.
Figure 12B:
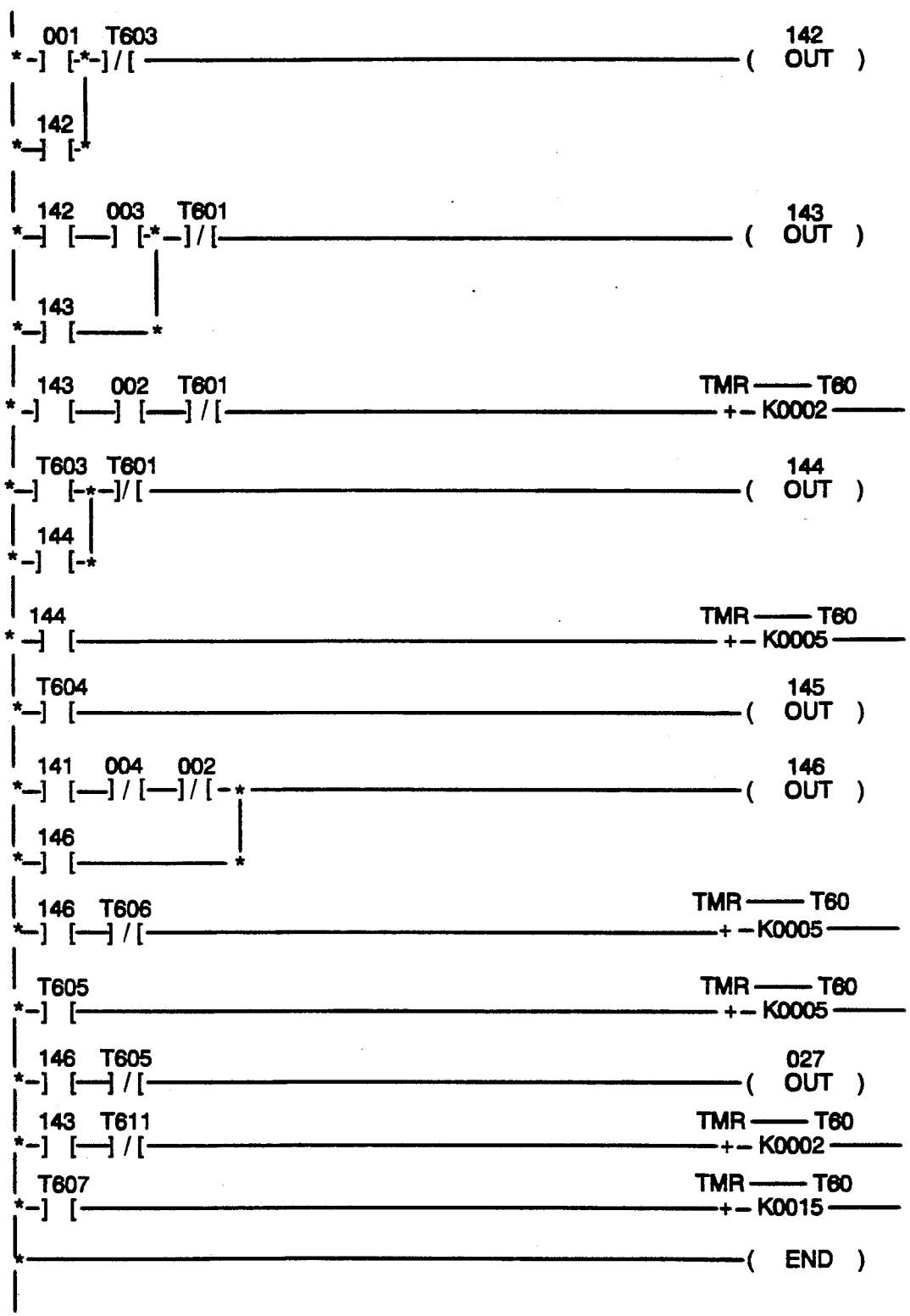

The program for PLC 250 (GE Model IC 609SJR100) is shown in ladder logic in FIG. 12. Table I is a program legend identifying the electrical connections and functions of various inputs, outputs, coils and timers of PLC 250 in terms of the ladder logic of FIG. 12. The PLC outputs 20 through 24 are applied to the solenoids 520 through 524, respectively, of FIG. 11 to control the operation of the system. Both solenoids 523 and 525 of FIG. 11 receive the PLC output 23.

TABLE 1

| PROGRAM LEGEND | |
|---|---|
| INPUTS | |
| 0. | Main Power and Reset Switch - N.O. |
| 1. | Forward Hall Effect Switch 321 - N.O. |
| 2. | Home Hall Effect Switch 323 - N.O. |
| 3. | Operator Push Button 104 - N.O. |
| 4. | Vacuum on Switch 315 - N.O |
| OUTPUTS | |
| 17. | Load Cell Data Release |
| 20. | Main Air Solenoid 520 |
| 21. | Band Cylinder Supply Shuttle Solenoid 521 |
| 22. | Band Cylinder Function Stroke Supply Solenoid 522 |
| 23. | Vacuum Supply Solenoid 523 and 525 |
| 24. | System Exhaust Solenoid 524 |
| 25. | Vacuum Go Lamp |
| 26. | No Vacuum Seal Lamp |
| 27. | Error Lamp |
| COILS | |
| 140 | Start or Reset Sequence |
| 141 | Return Request |
| 142 | Function Cycle Staged |
| 143 | Function Cycle |
| 144 | Delay Zero Cycle Latch |
| 145 | Zero Queue |
| 146 | Error |
| 374 | First Scan One Shot |
| TIMERS | |
| 601 | Zero Timer 1.0 Second |
| 602 | Cancel Forward Request 5.0 Second |
| 603 | Transmit Data .2 Second |
| 604 | Delay Zero .5 Second |
| 605 | Error Light Blinker On .5 Second |
| 606 | Error Light Blinker Off .5 Second |
| 607 | Data Dump Counter 1.5 Second |
| 611 | Cycle Timer for 607 |

While a preferred embodiment of the invention has been illustrated, it will be appreciated by those skilled in the art that various modifications and changes may be made thereto without departing from the scope of the invention as defined in the following claims.

What is claimed is:

1. An apparatus for measuring a force required to remove from an object a flexible seal adhered substantially in a plane to the object, said apparatus comprising:
   means for fastening a portion of said flexible seal to a stationary portion of the apparatus;
   means for removing said flexible seal at a predetermined angle by moving said object away from said fastening means in a substantially straight line at an angle equal to one-half of said predetermined angle with reference to said plane, said predetermined angle being greater than 0° and being selected to simulate flexible seal removal by a human;
   means for measuring a force applied by said flexible seal to said fastening means during movement of said object away from said fastening means.

2. An apparatus in accordance with claim 1 wherein said measuring means includes means for measuring the tensile force acting upon said flexible seal at said predetermined angle with reference to said plane.

3. An apparatus in accordance with claim 1 wherein said measuring means includes means for repeatedly measuring the force applied to said fastening means by said flexible seal during said movement of said object.

4. An apparatus in accordance with claim 1 wherein said measurement means includes means for repeatedly measuring the force applied to said fastening means by said flexible seal at selected distances along said flexible seal during said movement of said object.

5. An apparatus in accordance with claim 1 wherein said flexible seal removing means moves said object at a substantially constant velocity and wherein said measuring means periodically measures the force applied to said fastening means by said flexible seal at regular time intervals to achieve measurement of said force at equal distances along said flexible seal.

6. An apparatus for measuring a force required to remove, at a predetermined angle approximately equal to 45°, a portion of a flexible seal adhered to a planar opening of an object, said apparatus comprising:

gripping means for attaching a non-adhered portion of said flexible seal to a stationary portion of said apparatus;

means for moving said object in a substantially straight line away from said gripping means at one-half of the predetermined angle with respect to said planar opening of said object whereby at least a portion of said flexible seal is separated from said opening; and means for measuring the force applied to said gripping means by said flexible seal at said predetermined angle with respect to said planar opening of said object.

* * * * *